(12) United States Patent
Kurunmäki et al.

(10) Patent No.: US 7,717,827 B2
(45) Date of Patent: May 18, 2010

(54) METHOD AND SYSTEM FOR CONTROLLING TRAINING

(75) Inventors: Veli-Pekka Kurunmäki, Jyväskylä (FI); Sami Saalasti, Jyväskylä (FI); Aki Pulkkinen, Tikkakoski (FI)

(73) Assignee: Firstbeat Technologies Oy, Jyvaskyla (FI)

(*) Notice: Subject to any disclaimer, the term of this patent is extended or adjusted under 35 U.S.C. 154(b) by 105 days.

(21) Appl. No.: 12/223,701

(22) PCT Filed: Mar. 5, 2007

(86) PCT No.: PCT/FI2007/050117
§ 371 (c)(1),
(2), (4) Date: Aug. 6, 2008

(87) PCT Pub. No.: WO2007/099206
PCT Pub. Date: Sep. 7, 2007

(65) Prior Publication Data
US 2009/0069156 A1    Mar. 12, 2009

(30) Foreign Application Priority Data
Mar. 3, 2006    (FI)    .................................. 20065147

(51) Int. Cl.
*A63B 71/00*    (2006.01)
(52) U.S. Cl. ............................... 482/8; 482/1; 482/901; 434/247
(58) Field of Classification Search .................. 482/1–9, 482/900–902; 434/247; 600/300; 601/23
See application file for complete search history.

(56) References Cited

U.S. PATENT DOCUMENTS 5,890,997 A    4/1999    Roth (Continued)

FOREIGN PATENT DOCUMENTS

EP    1159989    12/2001

(Continued)

*Primary Examiner*—Glenn Richman
(74) *Attorney, Agent, or Firm*—Fildes & Outland, P.C.

(57) ABSTRACT

The invention relates to method and system for controlling a training plan for a user having a chosen aim for training, where
- at least one parameter describing physical characteristics of the user is determined, and
- a training plan consists of plurality of days, each day having one or more training sessions or rest, and
- each performed and coming session having a training load described by one or more parameters
- a training template is determined according to the aim and the said one or more parameters describing physical characteristics, each training template having a cumulative training load target according to the said parameter and the chosen aim and consisting of one or more training sessions or rest in each day, each training session of the template having a pre-selected training load, and
- an adapting window is determined, the adapting window consisting of a plurality of days, which include one or more previous sessions and one or more coming sessions according to the training template, and
- training loads of each session in the adapting window are combined into a cumulative training load, which is compared relatively to the cumulative training load target in the template, and depending on the comparison one or more coming sessions in the adapting window are adapted by changing one or more training loads of these so that the performed training load and the training load of the coming sessions as a combination meets the cumulative training load target.

28 Claims, 12 Drawing Sheets

U.S. PATENT DOCUMENTS

Figure 1:
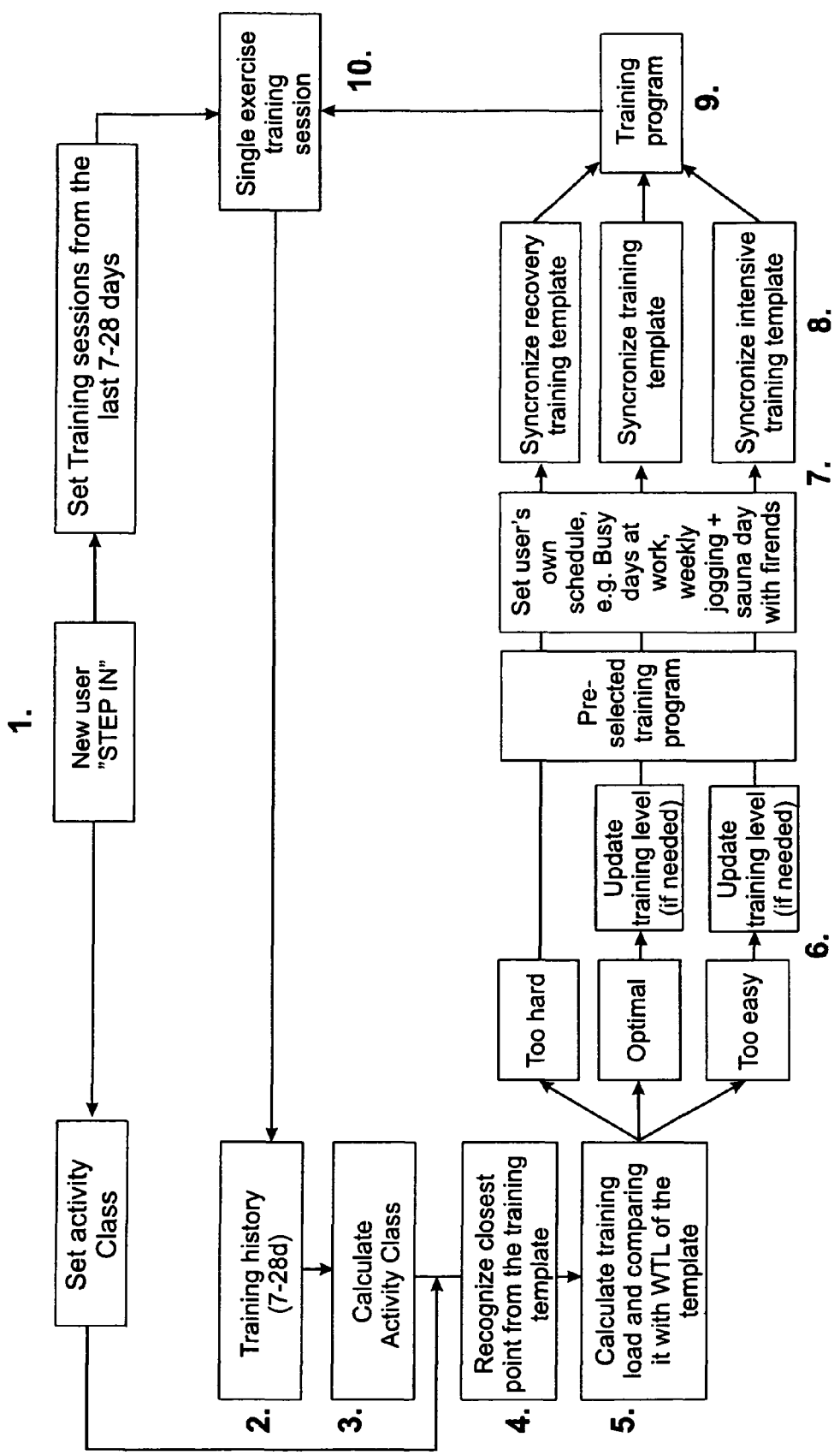

| | | |
|---|---|---|
| 6,749,432 B2 * | 6/2004 | French et al. ............... 434/247 |
| 2002/0072655 A1 | 6/2002 | Pfeffer |
| 2007/0219059 A1 * | 9/2007 | Schwartz et al. ............... 482/8 |
| 2007/0224582 A1 * | 9/2007 | Hayashino et al. .......... 434/247 |
| 2007/0232450 A1 * | 10/2007 | Hanoun ........................ 482/1 |

FOREIGN PATENT DOCUMENTS

| | | |
|---|---|---|
| WO | 02/19603 | 3/2002 |

* cited by examiner

User performed training sessions

| 1 | TE 1.0-1.9 30min | Rest | TE 2.0-2.9 40min | TE 3.0-3.9 35min | Rest | Rest | Rest |
|---|---|---|---|---|---|---|---|
| | Mon | Tue | Wed | Thu | Fri | Sat | Sun |

Pre selected training program from training program bank

| 2 | TE 1.0-1.9 30min | Rest | TE 2.0-2.9 40min | Rest | TE 3.0-3.9 35min | Rest | Rest |
|---|---|---|---|---|---|---|---|
| | Mon | Tue | Wed | Thu | Fri | Sat | Sun |

User's own schedule

| 3 | Rest | Train | Train | Rest | Rest | Rest or Train | Rest or Train |
|---|---|---|---|---|---|---|---|
| | Mon | Tue | Wed | Thu | Fri | Sat | Sun |

Syncronized training program

| 4 | Rest | TE 2.0-2.9 40min | TE 3.0-3.9 35min | Rest | Rest | TE 1.0-1.9 30min | Rest |
|---|---|---|---|---|---|---|---|
| | Mon | Tue | Wed | Thu | Fri | Sat | Sun |

Fine tuning of the training program

| 5 | | TE 2.0-2.9 40min | TE 3.0-3.9 35min | Training load too low, readjust the program! This session harder | | TE 1.0-1.9 30min | Too hard / Optimal / Too easy |
|---|---|---|---|---|---|---|---|
| | Mon | Tue | Wed | Thu | Fri | Sat | Sun |

Final training program

| 6 | Rest | TE 2.9 40min | TE 3.7 35min | Rest | Rest | TE 2.5 30min | Rest |
|---|---|---|---|---|---|---|---|
| | Mon | Tue | Wed | Thu | Fri | Sat | Sun |

Fig. 4a

Fig. 11

METHOD AND SYSTEM FOR CONTROLLING TRAINING

BACKGROUND OF THE INVENTION

1. Field of the Invention

Invention relates for METHOD AND SYSTEM FOR CONTROLLING TRAINING PLAN OF A TRAINING PERIOD OF A USER.

In the method at least one parameter describing physical characteristics of the user is determined, and a training plan consists of plurality of days, each day having one or more training sessions or rest, and each performed and coming session having a training load described by one or more parameters a training template is determined according to the aim and the said one or more parameters describing physical characteristics, each training template having a cumulative training load target according to the chosen aim and consisting of one or more training sessions in each day, each training session of the template having a pre-selected training load.

2. Description of the Related Art

WO2005021107: PERSONNEL TRAINING SYSTEM AND METHOD (Steffan Klein, 2005); "System and method for virtual personal trainer in fitness training". One database includes primary instructions how to exercise based on which user may start to exercise. Heart rate monitor is used to evaluate fitness/activity level when further instructions, both visually and verbally, can be given from the database (intensity, duration of sets). This system does not plan future training, but rather is focused to the guidance of single training session.

JP2004054591: METHOD OF CREATING HEALTH PROMOTION PROGRAM AND METHOD OF EXECUTING HEALTH PROMOTION (INST OF TSUKUBA LIAISON CO LTD 2004)

User fills up questionnaires (e.g., food, lifestyle, fitness tests, exercise) based on which computer determined fitness-program. When the prescribed program is completed, execution is inputted in the computer which adjusts the next prescription. This system the prescription is fixed in nature and thus the new prescription is given only after the old one is completed, although conditions could be changed.

AU2002357966: MOBILE FITNESS AID (Siemens 2003)

Document discloses a mobile terminal, which sends information on the body to the receiver on which based on the information training prescription is build and sent back to mobile terminal.

EP1159989: A method of generating and/or adjusting a training schedule (In2sports 2001)

Encloses invention that includes system to give training prescription is based on human expert build database. The training schedule is updated according to electronically obtained parameters during training session. However, document does not disclose, how schedules are created in respect to personal characteristics and how they are changed according to the obtained parameters.

US 2005/0004436 A1: Method and device for weight management of humans.

Creates weight management programs based on initial weight and weight target which is modified with current weight, food intake and energy expenditure. This kind of system is not capable to control fitness training to improve fitness and thus does not present training schedule having training sessions.

EP 0650695 (Polar Electro) "Fitness index"

This document gives teaching about one way to determine individual's level of fitness. This method is based on mean pulse value during whole performance. Mean pulse value can be calculated for predetermined exercise sequences, which exercise sequences have some preferred workload. If a person is able to exercise a given same workload or sequence of workloads with lower heart rate average(s) than before, it means that his/her fitness has improved. Accordingly the patent publication EP 0650695 discloses a method and apparatus for evaluating fitness level of a person. The method can also be utilized to point out that a given level of average intensity has been achieved during a single training session.

WO 2004/016173 (Firstbeat Technologies Oy.) "Method for monitoring accumulated body fatigue for determining recovery during exercise or activity" (=US2006/032315 A1), which is incorporated herein. This document presents more accurate method for deriving information on exercise and physical activity induced changes in body fatigue. Particularly this document presents an accurate connection between the exercise parameters (intensity, duration) and the accumulated body fatigue effect. The accumulated effect is preferably scaled in a physiological quantity, and preferably in EPOC (excess post-exercise oxygen consumption [oxygen ml/body weight kg], This kind approach gives possibility to determine the physiological load of a single exercise more accurately.

US2006/0004265 A1 (Firstbeat Technologies Oy.) "System for monitoring and predicting physiological state under physical exercise", which is incorporated herein. This document presents widely a method to monitor physiological state of user during a physical exercise. Document concentrates mainly in real time monitoring and predicting a physiological state in one single exercise. However, it introduces useful terms and connections between them, like a scale for on EPOC based training effect and a practical relation between terms: EPOC, training effect and activity class.

Document refers shortly to Training-Session Planning and Monitoring for three following days in way where a training plan is always fixed in advance. Training plan should be changed manually e.g. in case a user feels session too hard.

SUMMARY OF THE INVENTION

The object of this invention is to achieve an improved method for controlling a training plan of for a user, in which method the training plan is automatically adapted and dynamically updated. This object is achieved with the features described in accompanying claim 1. The characterized features of the system according to the invention are described in claim 24. Adapting takes place preferably on a daily basis. The term "daily" here must, however, understand widely—even once a week may satisfy needs in certain embodiments. The training load target is preferably a range. Adapting takes place only if the said a cumulative training load stays relatively out of the range, where "relatively" refers to a case, where the adapting window has a different length as the template.

In the first embodiment the final plan is influenced by following parameters:

1. User aim (default=fitness improving)

2. User time target to achieve the aim (default 28 days to next training level) Cumulative training load derived from observed training sessions, from e.g. one week or month 3. Observed training sessions from previous training day or more to monitor how training has actually occurred and to synchronize a predefined training template from a training template bank to the user.

4. Physical characteristics describing the personal fitness level or activity level of the user 5. Predefined training template bank defined by expert.

6. User defined aim, e.g., whether to maintain, improve or improve dramatically fitness level, as well as weight drop or marathon.

7. User may input preferred training schedule for future training days, e.g., day which to train, which to rest or which the system can decide.

First, to make training plan for future, the effects of previous training to the body must be known. Therefore, in the best possible solution system requires a good measure for the training load, one parameter or one that describes the physiological exercise load for the given exercise. One favorable measure can be, for example, EPOC (Excess post-exercise oxygen consumption), which is a cumulative measure for training load. It also possible to take account of other information than exercise data only, such as information related to the recovery state of the person. Recovery state can be monitored based on, e.g., heart rate variability or parameters derived thereof.

Second, system creates automatically full training plan, for example, for the next week, which includes necessary information for the user to perform the exercise. This information includes, for example, which kind of exercise to perform each day (how strenuous and how long training session) thus including the optimal scheduling of training session within the week including also the possible resting days.

Third, system includes parameters that describe the user's fitness level and/or training phase. Based on the training sessions executed (training history), these parameters are updated. Based on these parameters, system adapts according to the user's training thus keeping the training plan optimal for the person: in a case of excessive training, easier training sessions or rest is planned and in the case of too easy training, more frequent and/or harder training sessions are planned. Furthermore, for example, if the planned training session is not executed and resting day or easier training session is performed instead, system adapts to this change and re-adjusts training plan to keep the optimal training rhythm.

Fourth, system includes training program database from which training plan is initially derived from and further modified according to previous training. Training program bank (database) contains preferably training templates suitable from beginners to athletes. User may however change or update this program database, for example, to training program database especially designed for marathon training.

Fifth, system parameters and thus the training plans are updated continuously, e.g., on a daily basis or after or even during every training session.

Sixth, system works in an essential automated fashion. This enable that the user neither need to have previous knowledge about training planning nor to manually make judgments about training. For example, system adapts to higher or lower training level (planning harder or easier training) according to how user is training to keep training plan suitable for the person. However, user has a possibility to input at which days he/she can exercise, cannot exercise or would like to exercise. This preferred schedule is taken into account when automatically generating the training plan and, for example, exercise is not planned for a day when user has no time to perform it.

Seventh, system can be in a wristwatch, mobile terminal, in a PC, fitness device or like, or any other comparable device able to receive and process the required automatically or user input data and give feedback to the user via instructions on screen or by synthesized or recorded speech. Optionally, system can receive data by manual user input.

Eight, system includes calculation procedure to adjust training plan. In the procedure, future training load based on training template is calculated and training template base training plan adjusted in an iterative manner so that the final training plan is set keep the training load within appropriate limits or at preferred level during planned training.

Ninth, based on observed training sessions, system recognizes the appropriate point in the predetermined training e.g., the appropriate training level or weekday and uses the training template in the predetermined training template bank thereof.

Tenth, system includes preferred, upper and lower limits in which cumulative training load must stay. These limits are dependent from the person's fitness or activity level.

As it is obvious for a person skilled in art, the system can also be implemented with some other measure, e.g., energy expenditure, duration and intensity, sum of heart beats, average heart rate, distance, speed, movement or other measure or user input, that describe the exercise session related to performance.

The invention and its embodiments are described more in detail with reference to following drawings.

Figure 2:
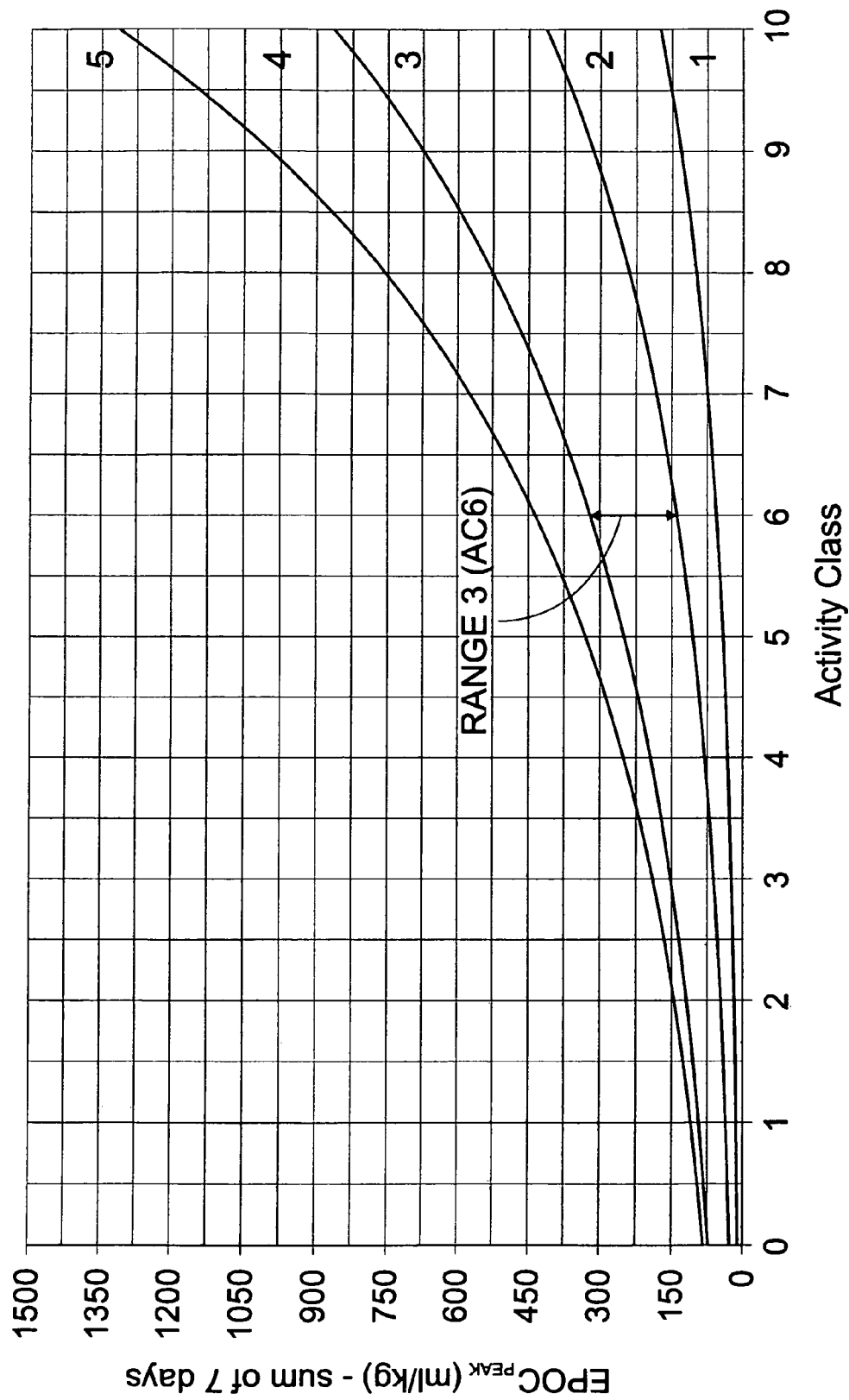

FIG. 1 presents system an overview according to the first embodiment of the invention FIG. 2 presents a cumulative measure for training load, e.g. Weekly Training Load (WTL)

Figure 3A:
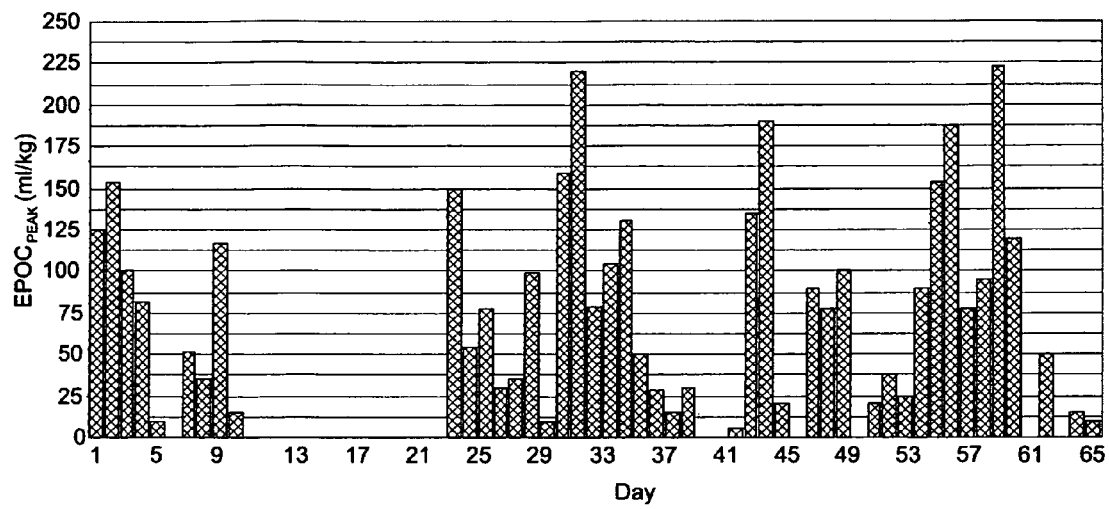
Figure 3B:
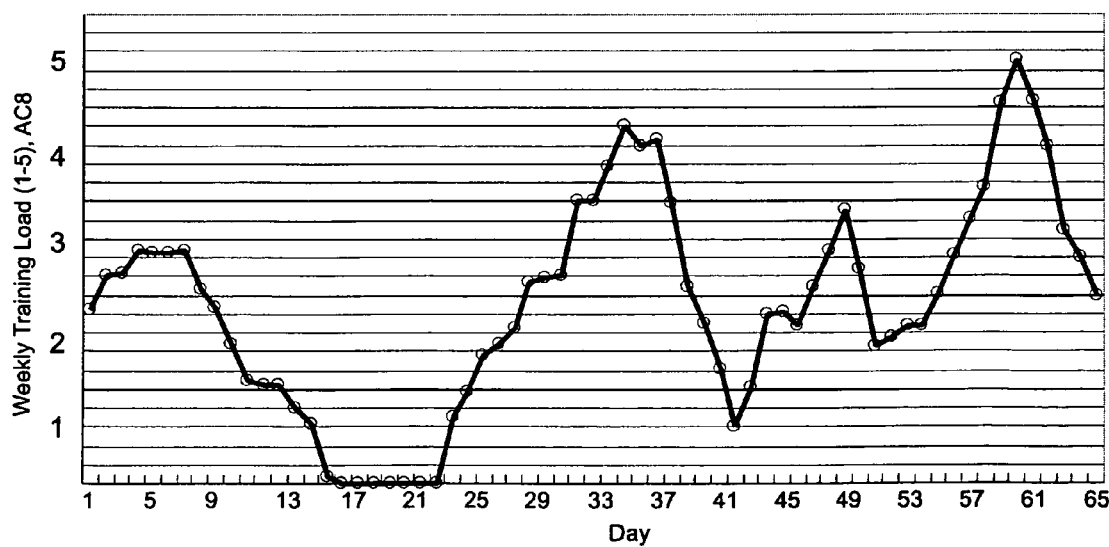

FIG. 3a presents an example of Weekly Training Load over 65 days of training, with EPOC-peak values FIG. 3b presents 7-days analysis window of data presented in FIG. 3a FIG. 4a presents an iterative process generating a training plan from desired and pre-selected training plans.

Figure 4B:
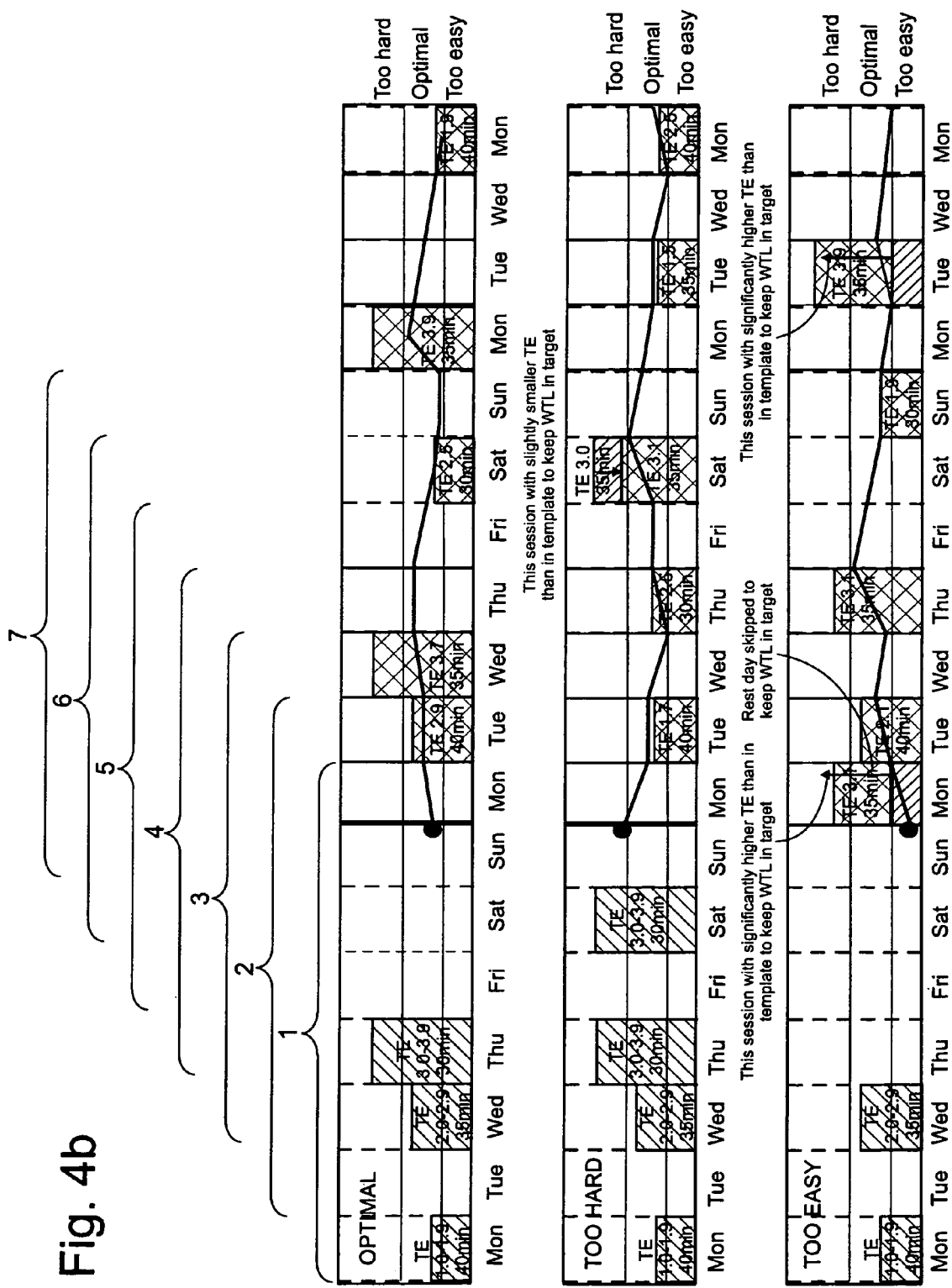

FIG. 4b presents examples effects of fluctuating weekly training loads (WTL)

Figure 5:
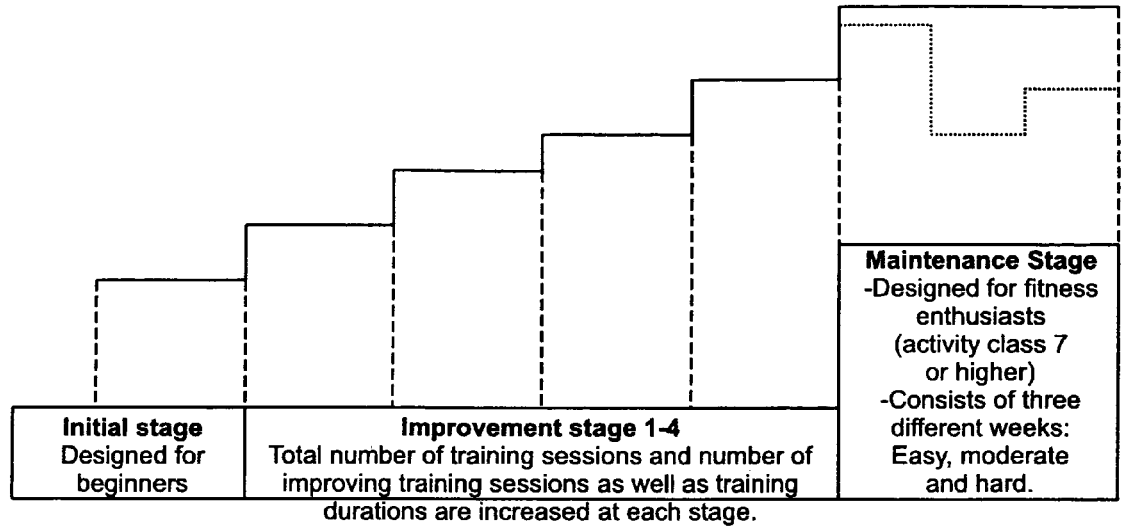

FIG. 5 presents training levels of another embodiment

Figure 6:
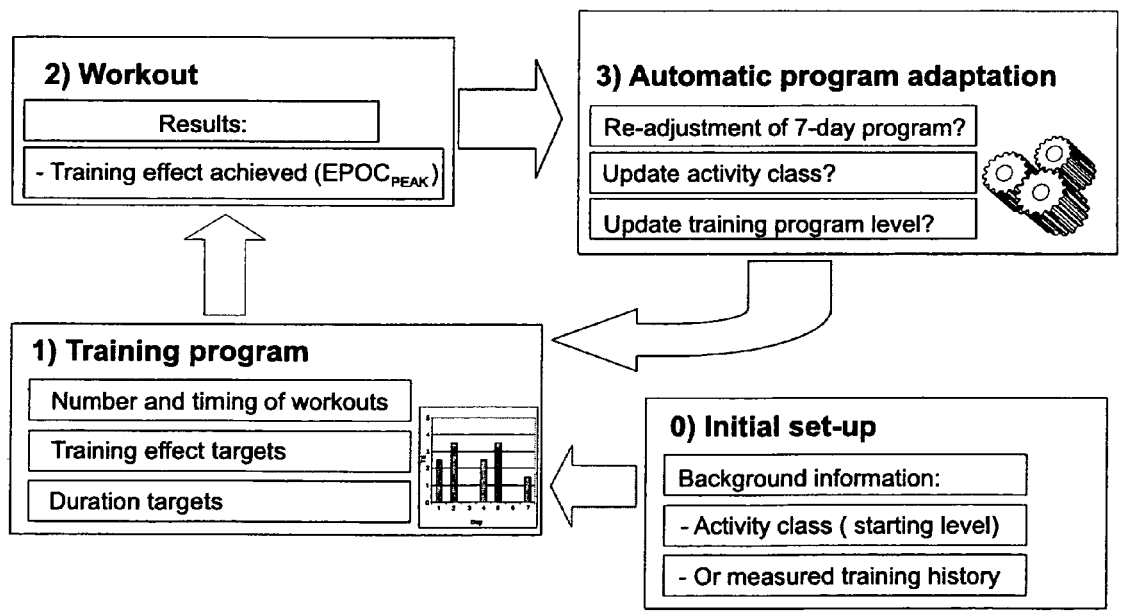

FIG. 6 presents a system flowchart schematically

Figure 7:
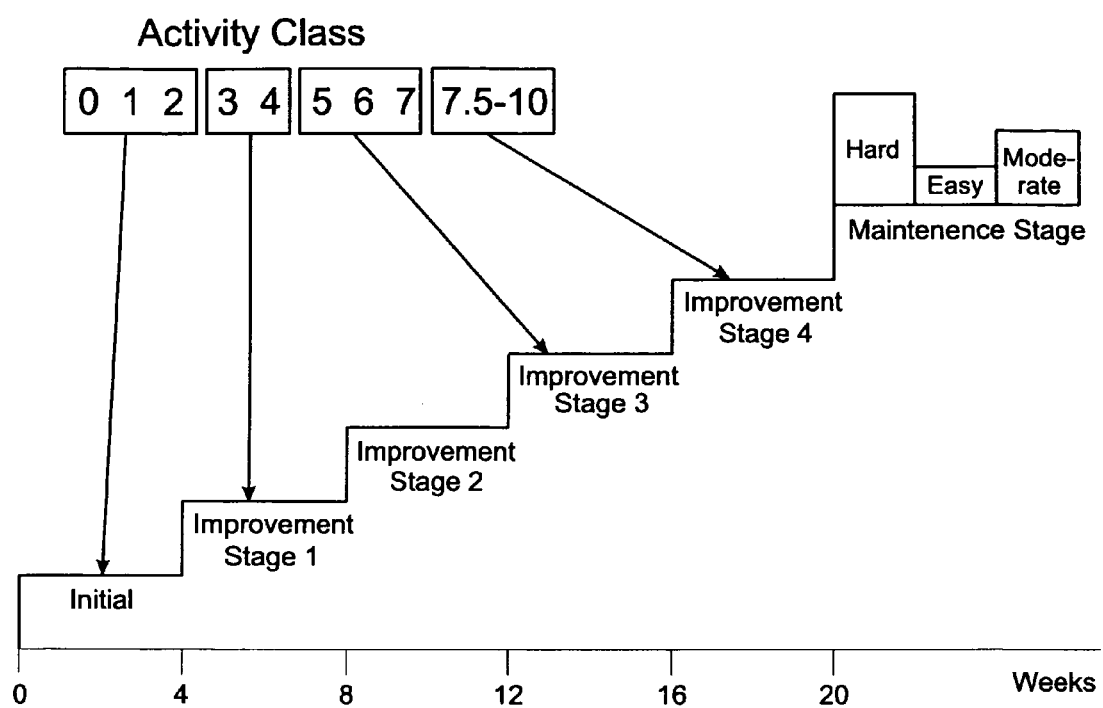
Figure 8A:
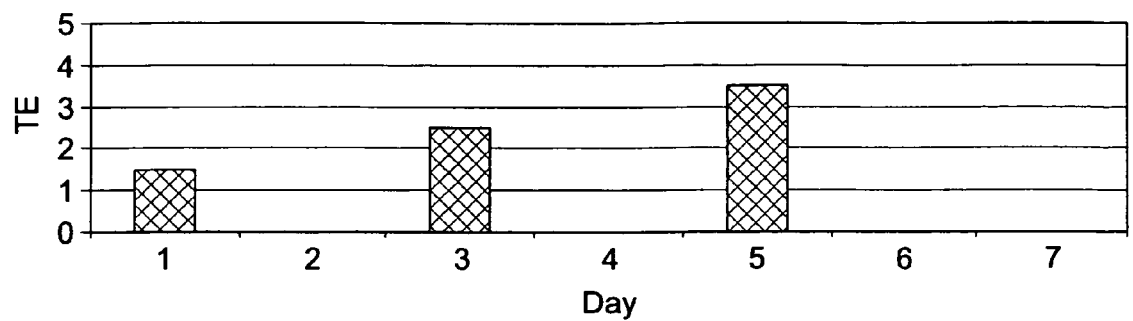
Figure 8B:
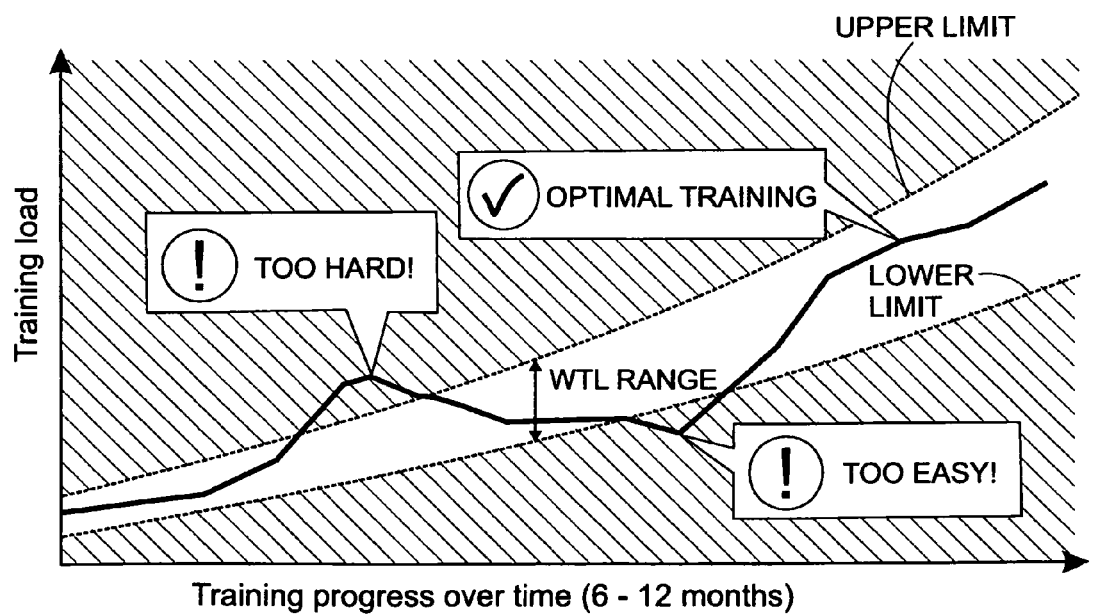
Figure 9A:
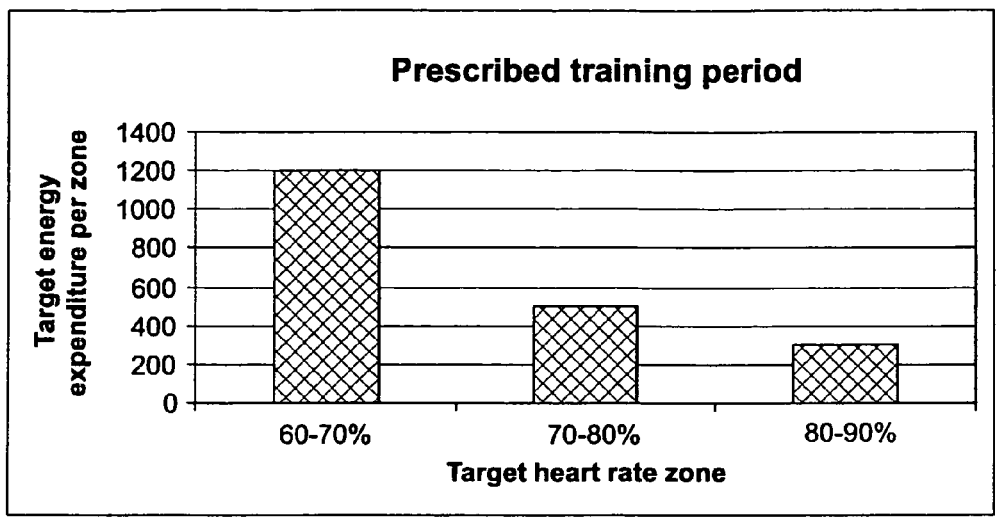
Figure 9B:
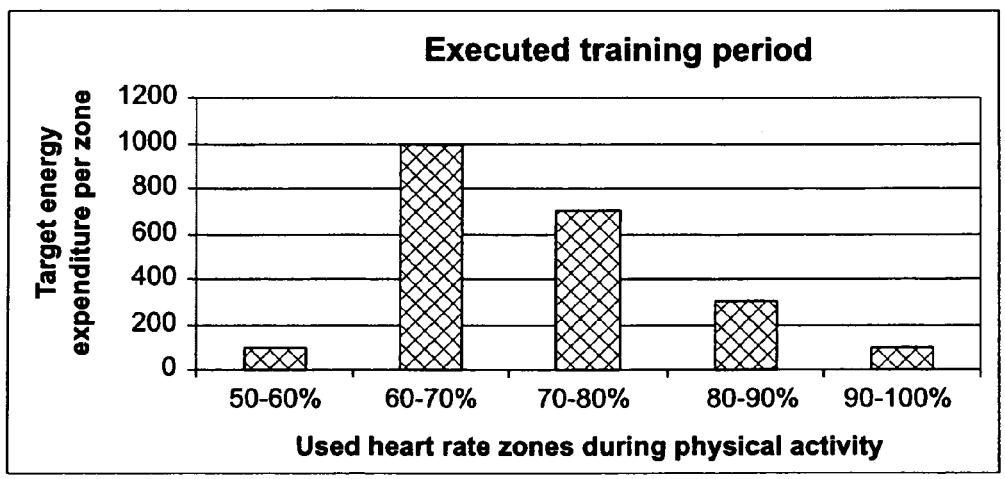
Figure 10:
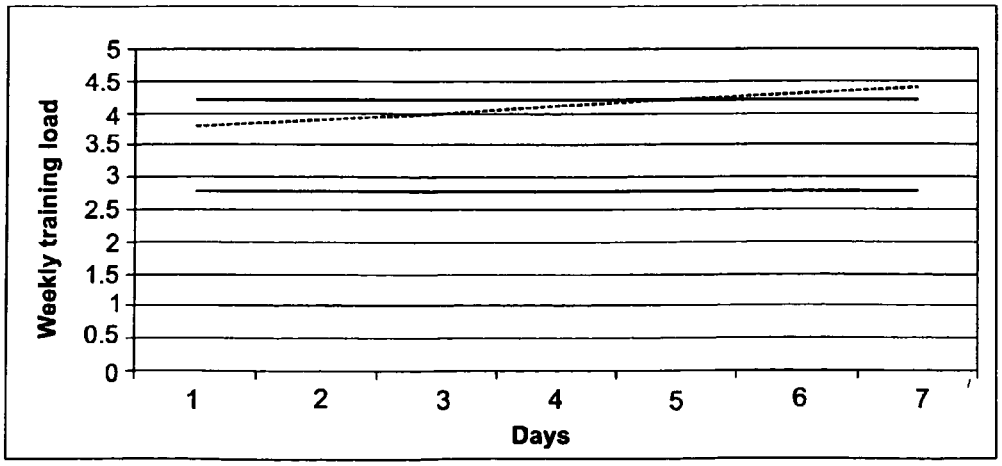
Figure 11:
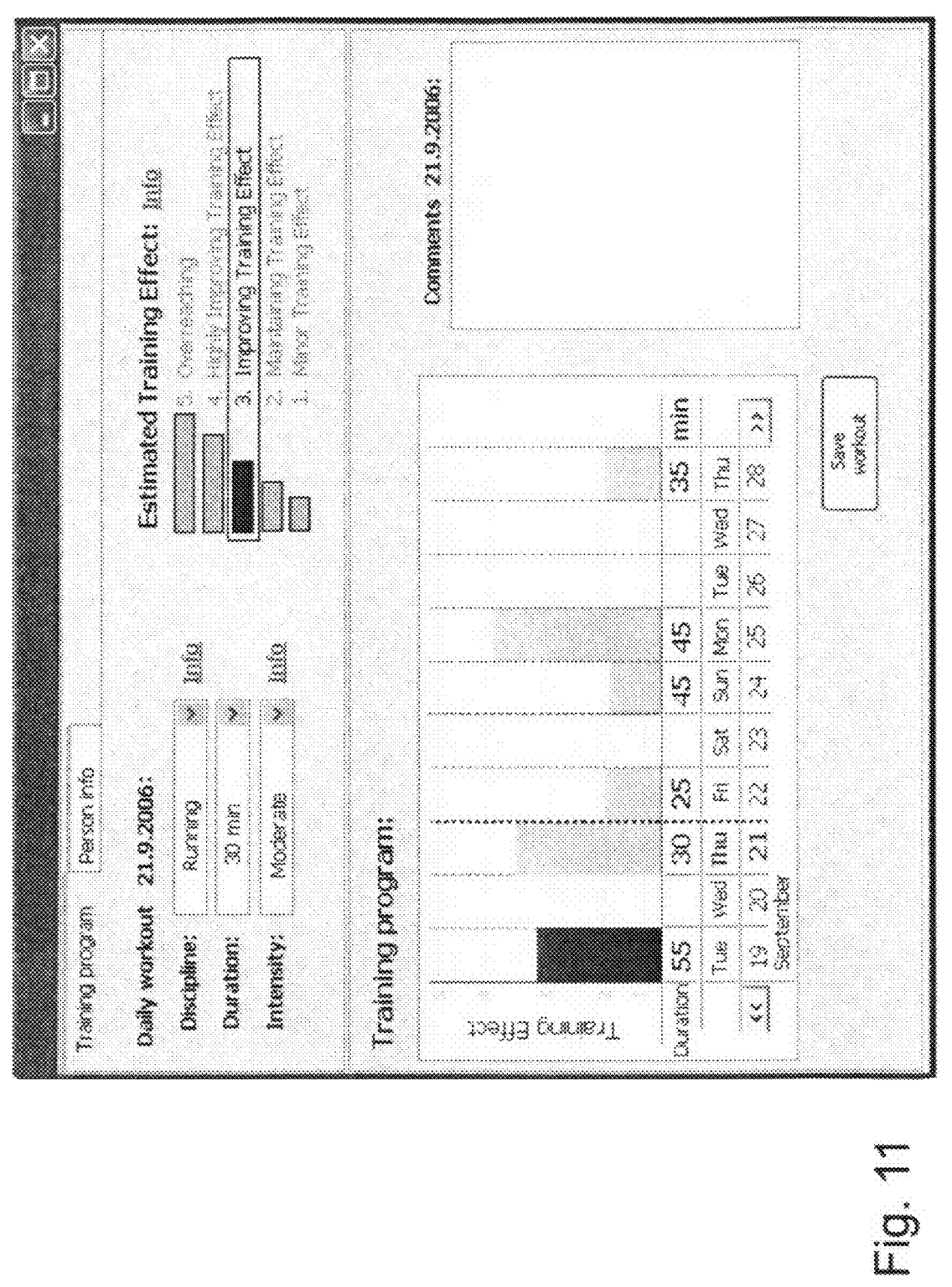
Figure 12:
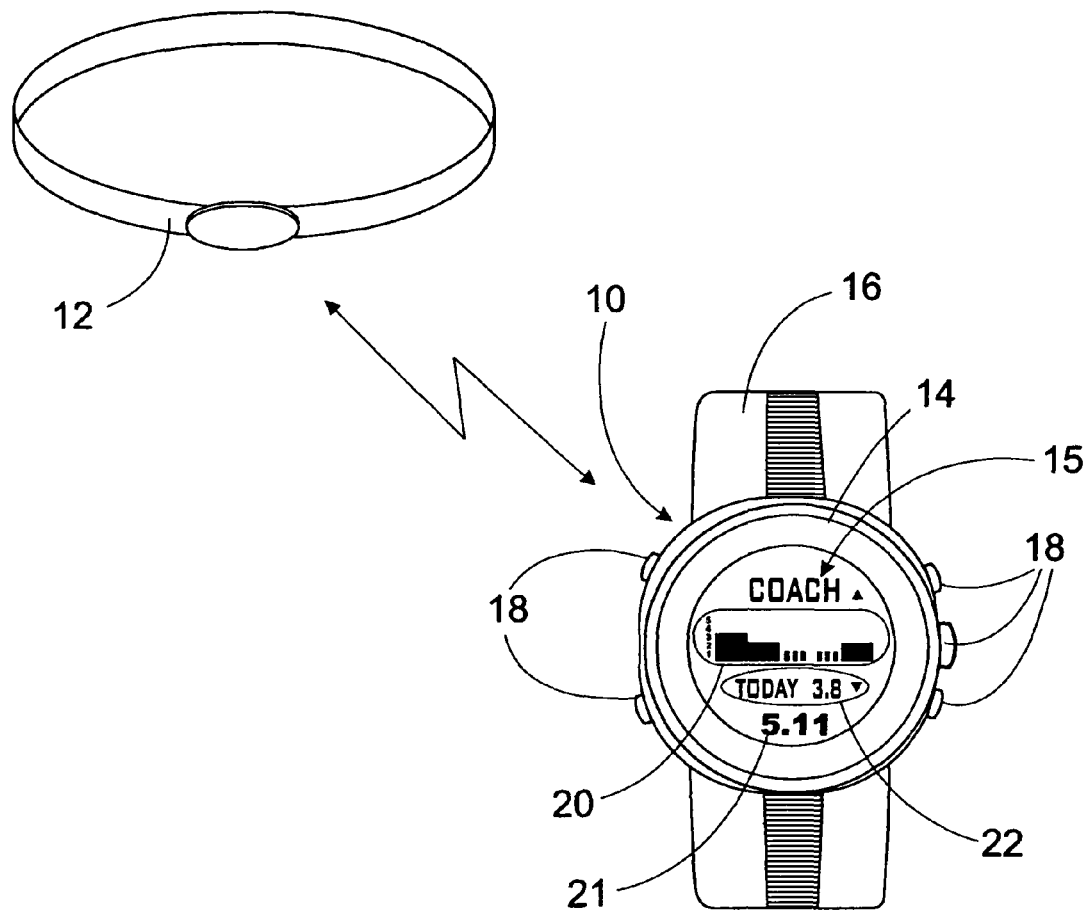
Figure 13:
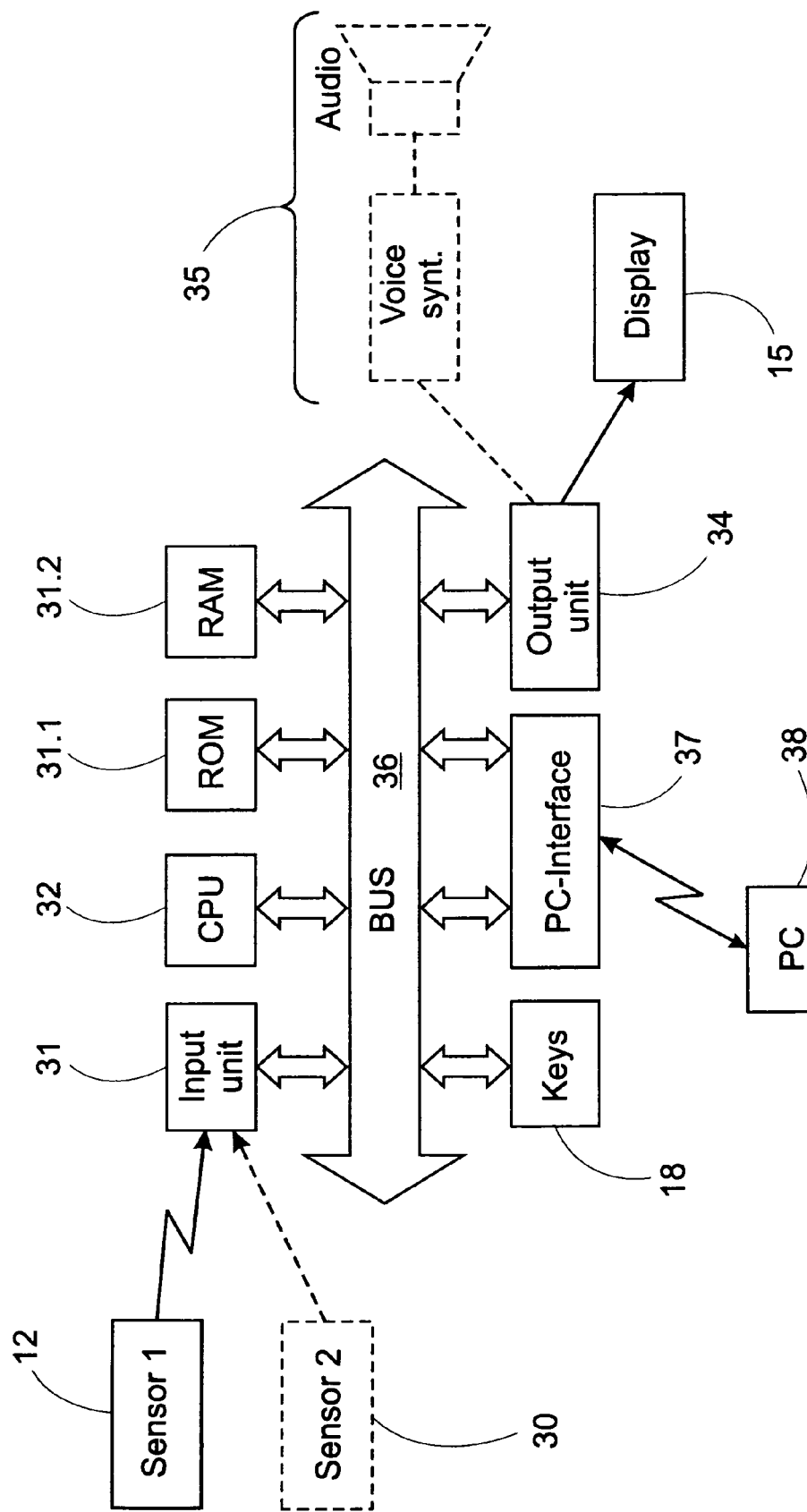

FIG. 7 presents relation of starting training level and activity class in one embodiment FIG. 8a presents an example of training plan at the initial stage FIG. 8b presents training development in a longer period and adjustments made based on actual training FIG. 9a presents an example of training plan FIG. 9b presents an example of performed training plan FIG. 10 presents personal training level during training week according to performed workouts in FIG. 9b FIG. 11 presents a screen of software application showing same period as in FIG. 9b FIG. 12 presents the main components of the system according to an embodiment of the invention FIG. 13 presents a block diagram of the system of FIG. 12 with additional interfaces.

DETAILED DESCRIPTION

System overview of one embodiment of the present invention is described below referring to FIG. 1.
1. The new user can "step in" to the system in two ways: By selecting his/her activity class or by entering his/her training sessions from the last 7-28 days into the system. If the activity class setup is used, the system continues configuring the training program from the step 3. Otherwise, system will analyze every training session (step 10.) and transfer training information to the training history (step 2.)
2. Training history collects information on training: Training frequency, training load, training duration, days trained in current training level, days trained in current activity class
3. User's activity class is calculated based on long term (28 days) training frequency, training load and days spend in current activity class
4. Based on the activity class (selected and calculated from the training history) and the physiological aim of the user, the optimal training template is automatically chosen to the user. Short time training history is used for determining the correct matching point from the training template. If no training has been performed training template starts from the very beginning of the chosen template.
5. Training load is calculated from the training history and is proportioned to the user's activity class, if only there is enough history information. If e.g. EPOC is used, training load is the sum of EPOCpeak values from the last seven days, e.g., weekly training load. According to the comparison "Too hard", "Optimal" or "Too easy"—procedure is selected.
6. Training load has a target range which is fixed or predetermined based on physiological aim of the user. Training load is optimal for the desired aim when it is within the target range. Otherwise training load is too hard or too easy. E.g., with weekly training load scaled from 1.0 to 5.0, optimal target range is between 2.8 and 4.2. If the training load is too hard (e.g. higher than 4.2), training level can't be changed. Otherwise training level can be increased or decreased, depending on the criteria required for each training level. Criteria are adequate training frequency, training load and activity class. Also the time spent in current training level has to be long enough. Pre-selected training template for each training level is an expert designed training program which is considered to meet the physiological aims set by the user. If training level does not change, the system continues to function with the same training template or any other template which fits to users physical characteristics. If training level is increased then the used training program template will be more demanding than before. On the contrary, if training level is decreased then the used training program template will be easier than before. Updating training level is optional and is not necessary in all embodiments
7. The user can add days when he/she wants to train and days when he/she doesn't want to train into the system. The system sets an appropriate day rhythm. The performed rhythm has precedence.
8. The system synchronizes the selected training template (step 4.) and user's own schedule (step 7) into one training plan. The system will recalculate the training load to the following days in a sliding window before giving the final training plan to the user (step 9). In the recalculation of training load, planned training sessions are adjusted to keep the training load at appropriate limits mentioned above. In case the training load has been too hard or too easy (step 6.), the training sessions are planned so that the training load can be restored to the target range.
9. Training program will be given to the user for the next 1-7 days or more. Training plans can be given e.g. in Training Effect-values and in recommended durations.
10. After the next single training session performed end recorded, training sessions are analyzed and data is transferred into training history (step 2). Then all the steps from 2 to 10 are repeated and performed again. This illustrates the dynamic nature of the training system.

Measure for training load can be e.g., weekly training load (WTL), calculated as the sum pf last seven day training sessions $EPOC_{peak}$ values proportioned to the user activity class to produce interpretable, 1.0-5.0 scaled weekly training load value. For example, 3.0-3.9 WTL means in Activity Class 6 a range of 145-315 ml/kg in $EPOC_{peak}$ scale, see FIG. 2. After this initial setting absolute training load values are not needed.

TABLE 1

Interpretation of weekly training load.

| | Weekly Training Load |
|---|---|
| 1.0-1.9 | Minor Training Load |
| 2.0-2.9 | Low Training load |
| 3.0-3.9 | Moderate Training Load |
| 4.0-4.9 | High Training Load |
| 5.0 | Overreaching Period |

An example of Weekly Training Load over 65 days of training is described in FIGS. 3a and 3b, wherein FIG. 3a presents $EPOC_{peak}$ for each day. FIG. 3b presents Weekly Training Load for each day based on the $EPOC_{peak}$ of last seven days or more generally, within a 7-day calculation window and the interpretation for different Weekly Training Loads.

Generally the training load is set in a scale of a cumulative physiological quantity, preferably a linear quantity. Training load can be estimated by at least one physical quantity of external workout (speed, time, length and/or power) describing the total physical load of workout. An accurate control is achieved when said cumulative physiological quantity is a parameter describing the general disturbance to homeostasis brought on by workout. This kind of parameter is EPOC (Excess Post-Exercise Oxygen Consumption) which is scaled linearly to Training Effect where the Training Effect is dependent on person's activity class. An example of the dependency between EPOC and Training Effect has been represented in US2006/0004265 A1 (Firstbeat Technologies Oy.) "System for monitoring and predicting physiological state under physical exercise".

EPOC peak values of weekly training sessions are summed to form Weekly Training Load value where the Weekly Training Load is dependent on person's activity class (see FIG. 2). The dependency between Weekly Training Load and person's activity class is preferably non linear, e.g. in the form:

Weekly training load=$ae^{bx}$, where e=2.71828, and where a and b are constants Due to the non-linear scale resolution is better in smaller activity classes.

FIG. 4a presents an iterative process, during which training plan is created by adjusting the predetermined training program in a way that the future training plan will keep the training load at the appropriate level: User has performed training sessions. A training template is used, selected from the training template bank based on the user's physical characteristics (e.g. based on user's activity class) and training level. Selected training template is synchronized based on the last few training sessions and user's own schedule. The final training plan is generated utilizing information of pre-calculated training load during the planned training: If training load is calculated to become too hard, required changes are made to make the training plan less demanding. If training load is calculated to become too low, required changes are made to the final training plan to make training more demanding. If training load seems to stay within predefined target range, then previously synchronized program is used as the final training plan.

Stepwise explanation of iterative process in which final training program is created. Each number refers to step in FIG. 4a:

1) User's training sessions in a previous week that he/she has performed are taken into account.
2) Predetermined training template (according to Activity Class) from training template bank is selected as a starting point for training plan. This template is then adjusted dynamically based on observed training.
3) User has possibility to set his/hers own schedule into program. This is taken into account.
4) Synchronized training plan is formed based on predetermined training bank base (point 2), which is modified by taking into account user preferred schedule (point 3), and by taking into account training sessions that user has performed (point 1).
5) Future training load, e.g., weekly training load, is calculated based on synchronized training plan (point 4).
6) Each planned future training session is modified to adjust the training load in such way that it stays within fixed or predetermined limits and tries to pursue towards the optimal training load level, e.g., training load stays within weekly training load limits 2.8-4.2 and tries to pursue towards weekly training load level 3.5. This process is done in an iterative manner in order to stepwise adjust the training load accordingly.

In FIG. 4b there is illustrated the effect of performed training workload in previous week. The sliding window (for days 1-7) is depicted by brackets. Each window calculates the training workload of the last day. All three schedules presents sessions in the previous week and coming sessions. The performed weekly training load is a black dot in each schedule on the end of Sunday. Now depending on previous week's WTL, next week's schedule is easier or harder to direct the total workload to optimum.

When weekly training load deviates from the target range, training plan is adjusted in the following way:

Training Load is Too High:

The next training session is chosen normally from the template. If the training session is too hard to decrease the WTL to the target range, template is changed so that target WTL range can be reached. The workload of the training session is decreased stepwise until the WTL is possible to restore to the target range. If it is not possible to restore WTL back to the target range at any given training session, rest is prescribed to the training plan. Based on the prescribed training session/rest the new "match point" from the training template is selected and training plan for the next days is created using this match point from the template. The same procedures are done after every training session in training plan.

Training Load is Too Low:

If the training session from the template is too low to reach target WTL range, template is changed. The same logic described above in the case "Training load too high" is used in opposite way. One exception is that the highest possible training session can't be higher than highest training session used in the training template (even if it would not be hard enough to restore the WTL back to the target range). That "rule" is used to keep training plan safe and for avoiding too hard training sessions.

Training Load is Optimal:

If the WTL is in the target range, training load of each session from the template is fine tuned within a given range described in FIG. 4a. For example: range can be 3.0-3.9 describing improving workout. Training load targets for each session are fine tuned in a way that WTL is kept in the middle of target WTL range.

System generates exercise plans, guiding the user to improve fitness via safe and effective training program. System contains six different training levels: initial stage, improvement stages 1-4 and maintenance stage (see FIG. 5). Training program template, in which training plans are based on, is different within each training level. Training plan is given for the next seven days, but the training plan is updated on a daily basis depending on the training sessions performed by the user (see FIG. 6).

System is designed for all people interested in improving fitness ranging from previously untrained to fitness enthusiasts. This is possible because of the different training levels. Before starting to train with system, the user has to define his/her activity class. Activity class determines the starting level described in detail in FIG. 5. Every training level has certain goals to be achieved before proceeding to the next level. In that way it can be ensured that training history and fitness level are adequate enough to carry out the next training level. Training plan is not either strictly tied to a certain sport. The users can freely select any endurance type exercise mode to achieve the training effects set by the system.

FIG. 6 shows, how the system works in practice. After entering the initial background parameters (0) training plan is created (1), which updates on a daily basis based on the training sessions performed by the user (2). Activity class, training level and template based training plan for the next 7 days are updated if necessary (3). Planned training program parameters can be transferred to goals of single training sessions, e.g., for preset course to this training session, user is then guided throughout the workout with feedback to achieve the goals coming from the training plan.

In the system according to another embodiment, training plan is given as EPOC- and TE-values, so the training sessions are not tightly restricted with respect the intensity and duration. This enables freedom to the user to decide how much time exactly he/she wants to spend in training. The user must just fulfill the goals set. However, system provides also recommendation about the preferred exercise duration. This assures that e.g., beginners are able to start training in a best possible way. EPOC, thus TE-values describe the true physiological impact of the workout to a body and the training effect gained. Generally the scale should be in units describing the impact of the performed workout to the physical fitness.

If the real time training effect (US2006/0004265A1; Firstbeat tech.) is also available, the training effect and time goal generated by the system can be set as targets for the given training session. It is then possible to guide the intensity of the exercise to reach the training effect goal in the time set. However, real time monitoring is not necessary at all, in an extreme embodiment most or all results of the performed training sessions are entered manually into system. These results may be in an external form, e.g. external power+time, running speed+time. These results can be converted into the $EPOC_{peak}$-scale using a specific conversion table with Activity Class. This is possible because both running speed or external power can be also used to calculate intensity (% VO2max). User may calibrate conversion values of his usual training workout using the real time monitoring. Calibration means in these cases measurement of maximal external work capacity, i.e. maximal aerobic speed or maximal power (Watts). Calibration enables more accurate intensity calculation which intensity estimate can be used to calculate EPOC, Training Effect and Weekly Training Load, or other training load values.

Manual entering of the performed workouts would be convenient if user e.g. forgets the wrist top or its HR-belt when having an exercise.

Training plan is not static but updates based on the training sessions user has performed. This assures the optimal training rhythm in all situations, regardless if the user hasn't been training according to training template during the last days. By doing this, the user will never be dropped of from the training program e.g., due to reasons like illness or busy schedule at work. System is also very safe training tool: It recognizes too heavy and too easy training periods by controlling the weekly training load. By this, overtraining and decreases in fitness-level can be avoided.

The user can also set his/her schedule to the training program. He/she can mark, for example, the days when he/she definitely wants to train and the days when there's no time for training and days when the schedule is free. System then takes these preferences into account when forming the training plan.

FIG. 7 shows that starting training level is based on the users activity class (AC). AC 0-2 starts their training from the initial stage, AC 3 and 4 from the improvement stage 1 and AC 5-7 from the improvement stage 3. Note that the user does not have to progressively proceed to the next training level but can also stay at the training level that best suits his/her personal goals. In this example the system contains eight templates each presenting own training level. AC determines the starting level and the starting template, the WTL of which is scaled according to AC.

In this example training levels and exercise programs are based on the American College of Sports Medicine's (ACSM) exercise prescriptions and training program. In ACSM program, training gets more demanding as the program progresses by increasing one or all of the frequency, the duration or the intensity of the training sessions. For example, from the initial stage to the improvement stage 4, the training frequency is increased from 3 training sessions per week to 5 training sessions per week and the duration of single training session from 25-35 min to 45-75 min, respectively. Training effects, training frequencies and durations for each training level are presented in table 2 in more detail.

TABLE 2

The number of training sessions with different training effect (TE) levels and the preferred durations of training sessions for different training levels.

| Training Level | Training frequency (times/week) | | | | Preferred training duration | |
|---|---|---|---|---|---|---|
| | TE 1.0-1.9 | TE 2.0-2.9 | TE 3.0-3.9 | TE 4.0-5.0 | Range | Total/week |
| Initial Stage | 1 | 1 | 1 | 0 | 25-35 min | 90 min |
| Improvement Stage 1 | 1 | 1 | 1 | 0 | 25-35 min | 90 min |
| Improvement Stage 2 | 1 | 2 | 1 | 0 | 30-60 min | 180 min |
| Improvement Stage 3 | 1 | 1 | 2 | 0 | 45-60 min | 210 min |
| Improvement Stage 4 | 1 | 2 | 2 | 0 | 45-75 min | 315 min |
| Maintenance HARD | 0 | 1 | 2 | 2 | 45-75 min | 300 min |
| Maintenance EASY | 2 | 2 | 0 | 0 | 30-60 min | 195 min |
| Maintenance MEDIUM | 1 | 1 | 2 | 0 | 45-75 min | 255 min |

Training program template and final training plan can be based on the weekly training load (WTL). Weekly training load is a sum of EPOC peaks from the last seven days. WTL is aimed to stay in a certain level or range. Training plans are given in training effect values. Wide range in EPOC-values between one training effect class (e.g., TE 2.0-2.9) makes it possible to adjust the WTL within the desired level.

In the background of the system, activity class is updated automatically based on the number of the training sessions and sum of the EPOC peaks from the last 28 days. When the activity class is sufficient for the next training level, training level can be changed providing that the user has been in a current training level at least 28 days. It is recommended that changes in training level would also require user's acceptance. That's because not everyone wants to improve their fitness all the time. Changes in training level could also be set manually. That's important when the user has selected his/her activity class wrong and the training program feels too demanding or too easy. Activity classes from 0-7 are based on the Jackson's classification. Activity classes from 7.5 to 10 are based on the VO2max values classification of the endurance athletes made by The Finnish Society for Research in Sport and Physical Education.

Before starting to train the user has to define his/her activity class. This can be done by selecting it from the list, filling a questionnaire or typing his/her own training history (EPOC peaks) to the program.

After typing the needed inputs, appropriate training templates are determined to the next seven days in TE-values with recommended durations. An example template from the initial stage is presented in FIG. 8a. According to the program the first training session is TE 1.0-1.9. If the user does harder training session, e.g., TE 3.4 instead of TE 1.0-1.9, training program moves to the next TE 3.0-3.9 point of the program and continues training plan from that point on. User's physical characteristics, e.g. fitness level influences to the determination of appropriate training template. User with higher fitness level has more demanding training template than a person with lower fitness level (WTL from FIG. 2). The timing of different training sessions is structured so that performed workouts give optimal benefit, i.e. weekly training load target is not meant to be reached with one overstraining training session but is reached by combining training sessions in a way that is physiologically meaningful. The rest sessions are a part of the training plan. During rest a body recuperates to receive a next training impulse.

The training development in a longer period (6-12 months) is shown in FIG. 8b, where a user's aim is the fitness improvement. The training template is more demanding when training continues. Each new template, after 28 days normally, has a bigger WTL (weekly training load) due to the higher Activity Class. However, when WTL is presented as a range, it gives some flexibility in weekly schedule. In the example shown in FIG. 8, WTL goes beyond the upper limit causing alarm "too hard" and easier training sessions (or even rest) are directed. When WTL goes beyond the lower limit, harder training sessions are directed and/or possible rest session is changed into a training session. The optimal training may fluctuate within the current range without affecting any change to template.

The idea of the recommended exercise durations is to guide the user to choose an optimal speed (intensity) to achieve target training effect in the time set. Target training effect can also achieved with freely chosen duration, in the case user wants to e.g., spend more time to exercise. However, for specific aims it is important to follow recommendations, e.g. for marathon, where user must run with a lower intensity.

Every training level has certain training goals to be achieved before being able to move to the next level. One criterion is a minimum duration, 28 days/training level. After the 28 days, training level can increase or decrease one step at the time, depending on the current activity class. Training plans are given from the training program planned separately to the every training level. The only exceptions in training planning will be made in the following situations:

Example: Training load of next training day can be TE 3.1, but the user has set his schedule to the program and the next day is actually set as resting day. In cases like that, user's schedule is with higher priority and the next day will be resting day. The TE 3.0-3.9 training session moves to the second day.

If the weekly training load deviates out from the range 2.8-4.2, training plan will deviate from the template: In case the WTL is over 4.2, program suggests rest or easy training sessions as long as WTL has dropped back in the target area. On the contrary, if WTL has dropped under 2.8, program suggests highest possible training effect (however, TE<3.9) for the next day(s) to rise the WTL back in the target area. NOTE: Rules described in the previous paragraph (1) passes over the rules in this paragraph (2). The whole training template from the initial stage to the maintenance stage will be get through in 28 weeks, if the training sessions have been performed according to the training plans. The last stage, maintenance stage differs a bit from the previous stages. It consists of the three different weeks: easy, moderate and hard weeks. That kind of periodization brings more variation to the training of the fitness enthusiasts.

Example of the input and output quantities.

Input:
  Peak EPOC (ml/kg) from the previous training session(s)
  Current Activity Class (0, 1, 2, 3, 4, 5, 6, 7, 7.5, 8, 8.5, 9, 9.5, 10)
  User's schedule for the next seven days: pre-selected resting and training days and days when rest or train (optional)
  Training level (optional)

Output:
  Training plan for the next seven days in TE (from 1.1 to 5.0) and/or EPOC peak (ml/kg)
  Recommended durations to the training sessions
  Updated activity class
  Updated training level
  Weekly training load (1.0-5.0)

In one embodiment, system consists of heart beat data collection device collecting users heart beat data during exercise and monitoring and analyzing and showing users exercise load on a e.g., wrist unit display. Heart beat data is automatically downloaded to PC or web service. User receives updated training program from PC or web service and training session information is automatically uploaded into wrist unit display. Based on this information, user may now easily execute training according to the training plan.

In other embodiment, similar to described above, but user does not need to download heart beat data into PC. Instead, the training plan control system is embedded into user's wrist-unit, mobile device or PDA.

Training load of a single session as well as cumulative training load can be derived from a plurality of physical parameters, by combining physical parameters with e.g. time. These include weighted sum of heartbeats (Training impulse=TRIMP), any combination of speed and time (e.g. distance), energy expenditure, combination of intensity % VO2max (or percentage of max speed) and time etc. Of course, these are not optimal ways to embody the described invention since these basic physical parameters are not directly related to the effects of training i.e. enhancement of fitness whereas $EPOC_{peak}$, training effect and weekly training load really are related to effectiveness of training.

In one embodiment of the invention single training sessions are planned by means of intensity combined with recommended duration distance or burned calories. Intensity can be measured e.g. as average heart rate or average speed. Distance covered or calories burned per week could in these cases serve as the measure of cumulative training load alone or could be combined with weekly training load.

In one embodiment the load of single training sessions is depicted by TRIMP and weekly cumulative load by 7-day moving average calculated from TRIMP.

In one embodiment of described invention a single planned training session consists of several exercises e.g. in the case of interval training. In this case the system is able to extract the number and intensity of physical activity periods and compare them to the plan. If e.g. the number of high intensity intervals during the training period is too low, missing interval training sessions result in harder planned training in the next training plan.

In one embodiment of the described invention training period may have two or more targets. In addition to fitness enhancement goal (executing training sessions in a meaningful order and achieving a given cumulative training load) there may also be a weight management or weight reduction goal. In the described embodiment the system internally plans single training sessions as $EPOC_{peak}$ or training effect values, and calculates weekly $EPOC_{peak}$ sum (weekly training load) but these are not necessarily shown to the user. Instead, only weekly energy expenditure targets for given meaningful intensity ranges are shown to the user as training plan, see FIG. 9a. This plan is modified based on history information (executed training sessions), cumulative training load, weekly energy expenditure and based on user's physiological characteristics. FIG. 9b represents a schematic case where user has performed a training period. Energy expenditure target has been slightly exceeded and the user has also executed training sessions with slightly higher intensity than have been planned. Also weekly training load has exceeded upper limit of its target value, see FIG. 10. Automatic system internally calculates next training plan (weekly program). In the described embodiment the system must not take into account the exceeded energy expenditure target since it is does not expose the user to overload; instead, if the user falls below cumulative energy expenditure target then the goal of next plan is to raise consumed calories back to target level. Instead of that, exceeding the weekly training load target causes the system to reduce the training load of next period. I.e. The energy expenditure target is similar next week, but calorie target is more distributed to lower heart rate zones. On the contrary, if user's energy expenditure would have been lower than the target, next period's energy expenditure target would be higher to keep the individual in his/her weight loss goal.

In one embodiment also the quantity and quality of user ingested food or only the amount of ingested calories can be inputted to the system. In this embodiment weekly energy expenditure target depens on the quantity of ingested calories. User can either directly input the number of calories he/she has ingested during a day or types in or selects quantity and quality of foods and/or portions that he/she has ingested. In the latter case the training plan control system must comprise a large database of different foods and/or portions which would enable calculation of ingested calories. In described embodiment the dynamic training plan comprises recommendations both on daily exercise and nutrition. Nutrition planning can also be provided to the user by means of changing daily menus. In this case the system must comprise a daily menu database including several expert designed menus where each daily menu consist of a given amount of calories. It is possible that the menu of upcoming days is provided to the user also by means of market shopping list to easen user's daily life.

The previously described embodiment could be implemented in a way that only daily training effect targets and recommended duration are provided to the user, where the combination of training effect and recommended duration is supposed to lead to the target energy expenditure. Training plan is updated based on whether the user has burned too small amount, too high amount or sufficient amount of calories, and based on user's cumulative training load, history information and user's physiological characteristics.

Since generally recommended amounts of energy expenditure (for weight management purposes) in physical activities have been acknowledged to enhance health, it is obvious for a man skilled in art that previously described embodiments can be applied also in combining fitness development goal and health enhancement goal.

In one embodiment of the described invention training plan can be provided by setting a target time to exercise in a given intensity range (heart rate range). Herein the main goal of the program is to enhance user's fitness. Calculation module is used to calculate $EPOC_{peak}$ or training effect during workout. Based on EPOC/TE values, the system plans appropriate training load for training sessions dynamically on a daily basis but these are not necessarily shown to the user. TE and duration targets provided by the system are transferred into time to exercise at (e.g. three) different intensities (e.g. heart rate ranges) over whole week. If user's weekly training load exceeds target, next period's training load will be reduced which is shown to the user as reduced time target in the higher end of heart rate ranges and increased time target at the lower end of heart rate ranges. If training load falls below the target then next period's target (WTL) will be increased to target level which is shown to the user as increased time target in the higher end of heart rate ranges and decreased time target at the lower end of heart rate ranges. In addition to weekly training load, also the history information on the order and difficulty of previous workouts will have an affect to next period's time-at-heart rate-range target. An example of described embodiment is shown in the table below. It is obvious for a man skilled in art that this embodiment can be applied also by using any other measure of intensity (speed range, oxygen consumption range, caloric burning rate range as kcal/min etc.

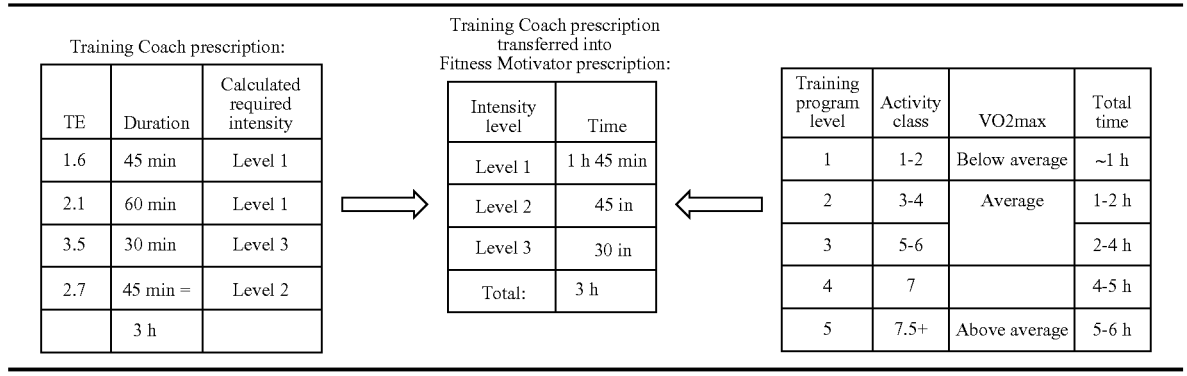

In one embodiment of the invention training plans and cumulative training load target ranges are set to prepare the user for running, skiing, a marathon or performing a triathlon. In this case each preparation phase (training level) has a specific training template base with a purpose e.g. to either build up endurance base, to build up fatigue resistance capability for a long race with high pace or to "taper", i.e. to trim the athlete during the last weeks before the main race. Similarly the target range of cumulative training load is set to support previous purposes. In addition, due to the long duration of previously mentioned events, it is possible to add a distance target to the plan (both daily plans and weekly target range). Distance target can be divided into one or more sport specific sub-targets, e.g. in triathlon program 10 km for swimming, 300 km for cycling and 70 km for running. If a user does not fulfill these targets, next predefined training program base will be adapted to put more emphasis to the discipline with too low distance in previous period. Similar sub-targets can be set also for e.g. $EPOC_{peak}$. Of course, it is also possible make duration or energy expenditure targets for different sports too. In one embodiment endurance base is enhanced in marathon (and ski marathon and triathlon) training programs with a combination of low cumulative (weekly) training load and high weekly distance. Fatigue resistance can be enhanced with high cumulative (weekly) training load and moderately high weekly distance. Tapering phase is characterized by both low cumulative (weekly) training load and low weekly distance.

In one embodiment of the invention it is possible to set a given fitness enhancement goal for a given period of time. I.e. user sets a goal to enhance her/his VO2max by 5 ml/kg/min or by 10% during two months. The system first decides whether the goal is realistic and if the goal is realistic, the system selects appropriate training level. Each training level has on or more training programs and each of the training programs has a target cumulative training load range. If the goal is not realistic, user must set a new goal. Whether the goal is determined realistic or not depends on the probability of reaching the goal. It is easier for a person with low fitness level to archive higher increase in fitness when compared to a person with low fitness level. The probability of reaching the goal also increases when the goal is set to a relatively low level and when the target date is set to relatively far in the future. The probability of reaching original longer term goals can be checked occasionally by the training plan control system by using a fitness test. If user's progress does not meet optional intermediate goals, original goal can be re-evaluated by the system. Of course, if user's goal setting is changed it also affects user's training plan. If user seems to lag behind intermediate goals this results in easement of training when compared with the plan that was assumed to be optimal according to original goal. If user's progress has been better than intermediate goals it is possible to either keep up in original plan or to slightly harden training when compared with the plan that was assumed to be optimal according to original goal. Naturally, the training plan control system can also function in reverse order. I.e. User inputs the number of workouts per week or month he/she is willing to train and the training plan control system then informs the user how much he/she is expexted to improve fitness level during a given period of time.

In one embodiment training level is updated based on user's fitness level. Fitness level can be evaluated by the system in one or several ways including: during normal training sessions, during separate fitness test or the user can input his new fitness level. Training plan control system can suggest meaningful dates for testing and calibrate future training plan based on user progress.

Calculation of EPOC, TE and cumulative training load requires information on exercise intensity during workouts. In one embodiment intensity is derived from user's heart beat information by using one or more heart beat derivable parameters where the heart beat parameter can be a measure of heart rate variability, heart beat frequency (beats per minute), respiration rate (breaths per minute), a measure describing increase/decrease/unchanging exercise intensity, or other similar parameter. In another embodiment of the invention the intensity of exercise is defined based on distance traveled, duration of exercise and user's physiological characteristics, such as fitness level measured as VO2max. This information may be gathered by means of global positioning (GPS) or accelerometry or by means of user input after the exercise. The user can define the intensity of exercise also by means of selecting a description of exercise which describes subjective feeling during exercise, e.g. "Moderate intensity" or "Training session required moderate breathing and perspiration" could correspond to an intensity of about 70% VO2max. Described intensity is used in the estimation of $EPOC_{peak}$, and consequently TE and training load (see FIG. 11).

In another embodiment of described invention the training plan control system prompts the user to exercise at times when there seems to be free time in user's schedule. User's schedule is evaluated base on his/her calendar markings. System also suggest a route to the user where the suggested route is selected from a route database consisting of user covered routes, or some other routes which have been performed by e.g. user's friend, or which have been downloaded from a website. Route can also be suggested based on suggested Training Effect and user's fitness level wherein higher fitness level affects towards selecting longer routes in a given time. The system can be implemented also by using distance suggestions only, which is easier to implement in devices with lower calculation and display capacity. System also takes into account the time required to transport the user to the place where training is performed. In a more sophisticated embodiment the training plan control system also takes into account environmental information in training plan. Environmental information include time of year (e.g. summer vs. winter), weather including snow conditions and ice conditions, road works etc. which all affect to the selection of suggested workout discipline (walking or running, biking, cross-country skiing, skating inline or in ice) or selection of route or both. The system can suggest several similar workouts from which user can select the best for him/her.

In another embodiment of described invention controlling training plan is performed by means of large expert-designed training template database (in ROM-memory or WEB-based database). The training plan can be given based on user's physical characteristics, history information, and current cumulative training load level wherein a given combination of these parameters produces some predetermined training plan in a deterministic way without adaptation phase.

In another embodiment of the invention the system first plans exercise session and then guides user throughout the exercise to reach the exercise target. Target can be e.g. to reach an improving training effect (e.g. 3.5) in available time. Target can also be e.g. to reach an improving training effect (e.g. 3.5) in the course of a meaningful route or distance. Target can also be e.g. to reach an improving training effect (e.g. 3.5) simultaneously with an energy expenditure target value, say 500 kcal. User can be guided during exercise using visual feedback (e.g. arrow), text, voice (speech messages) or vibration signals etc.

It is obvious for one skilled in art that any of the characteristics described above as possible embodiments can be combined, or some features can be left out in the scope of described invention.

The system according to the invention can be applied in many kinds of device. FIG. 12 shows an operating device 10 (wrist top device) with a heart-rate transmitter 12. This kind of hardware assembly was presented in document US2006/0004265 A1. However, new software is needed for this functional coach. The transmitter 12 is in radio contact with the receiver of the operating device 10. The invention is also suitable for use in connection with exercise devices, such as a stationary cycle or rowing machine. The invention can also be applied in connection with a mobile telephone (mobile station, or more generally a PDA device), for example, over a Bluetooth connection or simply over a wire connection. The application program is then implemented in the operating system (e.g., Symbian/Nokia® Series 60 or Windows CE). Generally the device is primarily personal, either fully portable or else connected to the exercise device being used. In the device (FIG. 13), there is a microprocessor 32 (CPU), a bus 36, a ROM memory 33.1, a RAM memory 33.2, and I/O means, such as a display 15 and a keypad or keys 18 as presented in FIG. 13. In the device there is also a connector (or wireless link) for a heart-rate monitor 12 or some other sensor that measures the intensity of exercise. The device may include also PC-interface 37. In the wrist top device itself, there can be, for example, a thermometer to depict the heat flow from the skin. Instead of PC also a mobile phone or a PDA-device could be linked to the wrist top device.

FIG. 12 show the operation of the wrist top operating device in greater detail. The operating device mainly corresponds to known highly developed operating devices of heart-rate monitors. in which there is a 'watch component' 14 held on the wrist by a strap 16, in the manner of a wristwatch. In it, there is a display device 15, particularly a graphic display unit, keys or buttons 18, the said heart-rate data receiver, and the processor component. Entry of the initial data and the target state takes place using the keys, using some logic that is, as such, known.

In the embodiment of FIG. 12, there are several numerical and graphic display fields (in either one or more physical fields) in the display device 15. The system according to this embodiment is able to calculate continuously the remaining part of the training workload, when session has started. The system shows the current training template in a graphic field 20 and today's session as a TE-value in text field 22 unless "Rest" is scheduled. User may change to a training display in order to follow the current training session. The time field 21 shows the elapsed time in the current session.

It useful combination that in addition to the functional coach the display device could show the output variable or all three according to above US-application publication (not shown).

According to FIG. 13, the system has as an input device a sensor 12 (e.g., a heart-rate monitor) measuring intensity. In addition to heart-rate measurement, it is also possible to use, for example, motion measurement (a second sensor 30), as shown by the broken line. In addition, in most applications, personal parameters are entered before using the device for the first time. The input data is led to the CPU 32 through an input unit 31. There are software means in the ROM memory 33.1 and the RAM memory 33.2 for its execution. From the CPU the data is led through the output unit 34 to an output device, which is, for example, a display 15. In addition or alternatively, it is possible to use a voice-synthesizer 35 with an audio-terminal device, to present the output variable (and even menus).

The training template database and/or the conversion table of external workouts are stored into the ROM memory 33.1. In another embodiment the PC-interface is used as a link to WEB-based service, where training templates can be downloaded from a WEB-server to the device. PC (or other linked device with a better user interface) may use for entering manually performed workouts.

In the next table there are presented a wide group of different "coaches" and their purposes. Each coach needs a specific template with a default training workload (WTL), which is scaled according to user's activity class or similar fitness characteristics.

|  | Training Coach | User need | Description |
| --- | --- | --- | --- |
| ALL AEROBIC TRAINING LINE | Beginner Coach | "I want to start to exercise regularly for my fitness and health" | Gives easy-to-start with dynamic training program. |
|  | Fitness Coach | "I'm already training regularly from 2 to 4 times per week, but how can I do my training more efficiently?" | Gives dynamic training program to improve fitness |
|  | Active Coach | "I train regularly. Occasionally, I compete in different endurance events." | Gives moderate to hard dynamic training program. User may select whether to improve, optimize or to maintain fitness. |
|  | Endurance Coach | "I train regularly. Occasionally, I compete in different endurance events." Especially I like long distance training and I have a lot of time available to train." | Gives moderate to hard dynamic training program with special reference to long duration workouts. User may select whether to improve, optimize or to maintain fitness. |
|  | Fitness Target Coach | "I can exercise n times per week and use x hours for that. How could I use my time investment with a best possible way?" | User may select time available to exercise and program gives estimate how much the user may improve with this time investment. Provides dynamic training program. |
|  | Active Target Coach | "I am preparing for competition held at dd/mm/yyyy and I want to be in good shape at that time." | User may set target when to be in shape and select to improve or maximize condition for target. Dynamic training program is provided. |
|  | Endurance Target Coach | "I am preparing for long distance competition held at dd/mm/yyy and I want to be in good shape at that time." | User may set target when to be in shape and select to improve or maximize condition for target. Dynamic training program is provided with special reference to long duration workouts. User may specify the duration of the upcoming race. |
| WEIGHT MANAGEMENT | Trim & Fit Coach | "I could loose few kilos of weight and would like to be fit." | Gives dynamic training program with also energy expenditure targets for targets for single workouts and for one week. User sets target weight. Designed for small weight reduction and maintenance. Weight input. |

-continued

| | Training Coach | User need | Description |
|---|---|---|---|
| | Weight Management Coach | "I want to loose weight." | Gives dynamic training program with also kcal targets. User sets target weight. Designed for moderate to large weight reduction. Weight input. |
| | Weight Management+ Coach | "I want to loose weight by both exercise and diet control." | Gives dynamic training program with also kcal targets and also recommendation about possible food intake as kcal with different options. User sets target weight. Designed for moderate to large weight reduction. Weight input. |
| RUNNING COACH LINE | 1st Marathon Coach | "I want to make it through my first marathon." | Gives dynamic training program with km to run based on which user can make it through his/her first marathon. User may set target time for marathon and day when marathon is held. Designer for target time 4 h or more. |
| | Marathon Coach | "I train to run a marathon with a target time." | Gives dynamic training program with km to run. User may set target time for marathon and day when marathon is held. Designed for target time up to ~3 h. |
| | Fitness Running Target Coach | "I can run n times per week and use x hours for that. How could I use my time investment with a best possible way?" | User may select time available to run and program gives estimate how much the user may improve with this time investment. Provides dynamic training program with distances to run. |
| | Running Target Coach | "I am preparing for running event held at dd/mm/yyy and I want to be in good shape for that." | User may set running event when to be in shape and select to improve or to maximize condition. Dynamic training program is provided with km distances to run. |
| | Running Target+ Coach | "I am preparing for running event held at dd/mm/yyy and I want to optimize my condition for that." | User may set running event when to be in a good shape and input target time for from 3 km to ½ marathon distances. Dynamic training program is provided with km distances to run. |
| | Fitness Running Coach | "Running is my hobby. I'm running regularly from 2 to 4 times per week, but how can I do my running more efficiently?" | Gives dynamic training program to improve fitness. |
| | Active Running Coach | "Running is my sport. I run regularly and sometimes with a training program, because I like to train sometimes hard. Occasionally, I compete in different running events." | Gives moderate to hard dynamic training program (TE, duration and distances to run). User may select whether to improve, improve much or to maintain fitness. |

The current template is changed to another in adapting only if the said cumulative training load stays relatively out of the range and current workload on the template cannot be changed within the pre-selected lower and upper limits in order to keep weekly training load in optimal.

The invention claimed is:

1. Method for controlling a training plan for a user having a chosen aim for training, where
   at least one parameter describing physical characteristics of the user is determined, and
   a training plan consists of plurality of days, each day having one or more training sessions or rest, and
   each performed and coming session having a training load described by one or more parameters
   a training template is determined according to the aim and the said one or more parameters describing physical characteristics, each training template having a cumulative training load target according to the said parameter and the chosen aim and consisting of one or more training sessions or rest in each day, each training session of the template having a pre-selected training load, and
   an adapting window is determined, the adapting window consisting of a plurality of days, which include one or more previous sessions and one or more coming sessions according to the training template, and
   training loads of each session in the adapting window are combined into a cumulative training load, which is compared relatively to the cumulative training load target in the template, and
   depending on the comparison one or more coming sessions in the adapting window are adapted by changing one or more training loads of these so that the performed training load and the training load of the coming sessions as a combination meets the cumulative training load target.

2. Method according to claim 1, characterized in that the training load is set in a scale of a cumulative physiological quantity.

3. Method according to claim 2, characterized in that training load is estimated by at least one physical quantity of workout describing the total physical load of workout.

4. Method according to claim 2, characterized in that the cumulative physiological quantity is a parameter describing the general disturbance to homeostatis brought on by workout.

5. Method according to claim 4, characterized in that the parameter is EPOC (Excess Post-Exercise Oxygen Consumption).

6. Method according to claim 1, characterized in that each training load is set between pre-selected lower and upper limits, which depend on at least one of said parameters.

7. Method according to claim 1, characterized in that the adapting window slides forward through a chosen number of days and adapting of the training template takes place in each position of the adapting window.

8. Method according to claim 1, characterized in that the cumulative training load target is a range having an upper target limit and a lower target limit, these limits depending on at least one of said parameters.

9. Method according to claim 6, characterized in that when the said cumulative training load stays relatively within the range the workload of next training session fine tuned in order get weekly training load in the middle of the range.

10. Method according to claim 1, characterized in that the adapting of the coming sessions includes adding rest instead of a scheduled training session, when the previous sessions were too hard or adding a training session instead of rest, when the previous sessions were too easy.

11. Method according to claim 1, characterized in that the training template consists of 7-28 days having at least one training session per 7 days.

12. Method according to claim 1, characterized in that at least one parameter describes physical activity of user during essential longer period than the training template.

13. Method according to claim 1, characterized in that method is integrated with controlling a real time training effect during a single training session.

14. Method according to claim 1 characterized in that a group of different training templates is determined initially corresponding different physical characteristics of the user.

15. Method according to claim 1, characterized in that the default training template is adapted according to user's aim with desired training days.

16. Method according to claim 1, characterized in that method is executed using remote processing, where personal data and each result of performed workloads are send remote system, which adapts training plan and send it to user.

17. Method according to claim 1, characterized in that method is executed using a local device having processing means for said adapting.

18. Method according to claim 1, characterized in that the parameters describing physical characteristic are updated automatically according each result of the performed training workload.

19. Method according to claim 1, characterized in that the aim of user is a weight control.

20. Method according to claim 1, characterized in that the aim of user is a marathon.

21. Method according to claim 1, characterized in that the aim of user is a rapid improvement of training level.

22. Method according to claim 13, characterized in that the dynamic guide is shown to the user as time to exercise in selected intensity range.

23. Method according to claim 22, characterized in that intensity range is described by one parameter belonging to the following group: heart rate level, speed, oxygen consumption, calorie consumption.

24. System for controlling a training plan for a user for training, where a training plan consists of plurality of days, each day having one or more training sessions or rest, and each session having a training load described by one or more parameters, where the system comprises a user interface device, comprising an input device for entering the values of initial variables describing physical activity and a personal aim for training and an output device for displaying information about at least the next session of training plan, and means for storing a group of training templates each presenting a schedule for training, each template corresponding different aim and/or a parameter describing physical characteristics and each training template having a cumulative training load target, and means for storing results of performed training sessions, and means for selecting a template according the aim and the physical characteristics of the user, and means for processing an adapting window having a plurality of days including at least one previous day and one coming day, and combining training loads of the performed training sessions and those of the template in the adapting window into a combination, and means for assessing the combination with the cumulative training load target, and adapting one or more coming sessions of the current template in the adapting window so that the combination meets relatively the cumulative training load target.

25. System according to claim 24, characterized in that system comprises wrist-unit with buttons and a display.

26. System according to claim 25, characterized in that wrist-unit has input means for receiving measured intensity of exercise and has means for controlling training session in real-time and for recording a result of each performed training session.

27. System according to claim 24, characterized in that system comprises PDA with keyboard and display.

28. System according to claim 20, characterized in that system comprises WEB-based system having a user terminal for sending data describing personal characteristics and results of previous sessions and receiving training template a server for receiving said data and processing a training plan using received data and sending it to the user terminal.

* * * * *